(12) United States Patent
Hobble et al.

(10) Patent No.: US 11,957,799 B2
(45) Date of Patent: Apr. 16, 2024

(54) GRAPHITE POWDER BASED COUNTER ELECTRODE

(71) Applicant: Garwood Medical Devices, LLC, Buffalo, NY (US)

(72) Inventors: Jackson Hobble, Buffalo, NY (US); Brian Peterson, East Aurora, NY (US)

(73) Assignee: Garwood Medical Devices, LLC, Buffalo, NY (US)

( * ) Notice: Subject to any disclaimer, the term of this patent is extended or adjusted under 35 U.S.C. 154(b) by 878 days.

(21) Appl. No.: 16/675,388

(22) Filed: Nov. 6, 2019

(65) Prior Publication Data

US 2020/0147245 A1 May 14, 2020

Related U.S. Application Data

(60) Provisional application No. 62/758,288, filed on Nov. 9, 2018.

(51) Int. Cl.
*A61L 2/03* (2006.01)
*A61L 27/08* (2006.01)
*A61N 1/04* (2006.01)

(52) U.S. Cl.
CPC ............... *A61L 2/035* (2013.01); *A61L 27/08* (2013.01); *A61N 1/048* (2013.01)

(58) Field of Classification Search
CPC .......... A61L 2/035; A61B 5/259; A61B 5/263
See application file for complete search history.

(56) References Cited

U.S. PATENT DOCUMENTS

| | | | |
|---|---|---|---|
| 3,936,318 A | 2/1976 | Cole, Jr. | |
| 4,109,648 A | * 8/1978 | Larke | ...... A61B 5/398 600/397 |

(Continued)

FOREIGN PATENT DOCUMENTS

| | | |
|---|---|---|
| JP | 2002525150 A1 | 4/2000 |
| WO | 2008067409 A2 | 6/2008 |
| WO | WO 2008/067409 A2 | 6/2008 |

OTHER PUBLICATIONS

International Search Report and Written Opinion for PCT/US19/60000; dated Mar. 30, 2020; 13 pages.

(Continued)

*Primary Examiner* — Alexander W Keeling
(74) *Attorney, Agent, or Firm* — Barclay Damon LLP

(57) ABSTRACT

A device for providing treatment is disclosed. The device provides proper skin electrical conductivity while still being minimally invasive by adhering to the patient's skin that also implements safety measures that off-the-shelf electrode options do not have. This device includes a graphite powder-based skin counter electrode that has a graphite powder suspended in an electrolyte gel that allows for electrochemical conduction between the graphite particles in the graphite powder. The gel is spread over a first side of a hydrogel layer. A device housing is mounted on the hydrogel layer over the first side. The device housing contains the electrolyte gel and graphite powder, defines an opening or lead opening as well as an empty expansion chamber for gaseous anodic byproduct. A metallic wire or rod extends from the electrolyte gel and through the housing opening and connects to a potentiostat. The second side of the hydrogel layer is adhered to the skin of the patient. The graphite powder-based skin counter electrode device takes into account safety.

13 Claims, 2 Drawing Sheets

(56) References Cited

U.S. PATENT DOCUMENTS

| | | |
|---|---|---|
| 4,846,185 A | 7/1989 | Carim |
| 6,309,535 B1 | 10/2001 | Williams et al. |
| 6,326,160 B1 | 12/2001 | Dunn et al. |
| 11,458,216 B2 * | 10/2022 | Ehrensberger ............ A61L 2/24 |
| 2004/0038090 A1 | 2/2004 | Faris |
| 2011/0308947 A1 | 12/2011 | Wilke |
| 2014/0294672 A1 | 10/2014 | Meyerhoff et al. |

OTHER PUBLICATIONS

Polyacrylamide/Graphite and Polyacrylamide/Titanium Dioxide Gel Electrodes; Lange et al.; Analytical Chemistry; vol. 58, No. 13; Nov. 1986; pp. 2875-2874 (3 pgs).

National Intellectual Property Administration of the People's Republic of China; First Office Action; Patent Application No. 201980073303.7; Issue Date: Feb. 17, 2023; dated Mar. 7, 2023; 3 Pages.

Supplementary European Search Report for EP 19 88 2130.8; Date Completed: Jun. 28, 2022; 7 pages.

Japanese Patent Office; Japanese Office Action; Patent Application No. 2021-525024; dated Sep. 6, 2022; 8 Pages.

* cited by examiner

| Ingredient | Amount/Concentration | Instruction |
|---|---|---|
| NaOH solution | 0.1-0.4M | Mix NaOH crystals with deionized water until fully disolved, heat to 40-60 degrees Celsius |
| Gelatin | 1g/25mL NaOH NaOH | Mix with NaOH solution for 1 hour |
| Electrolyte Gel | 1gram:1mL ratio with NaOH | Heat to 40-60 degrees Celsius and mix with NaOH for 30 minutes after gelatin has hydrated |
| Pure Graphite Powder | 1:10 ratio with Electrolyte Gel | Stir into electrolyte gel mixture until fully homogeneous |

*Fig.3*

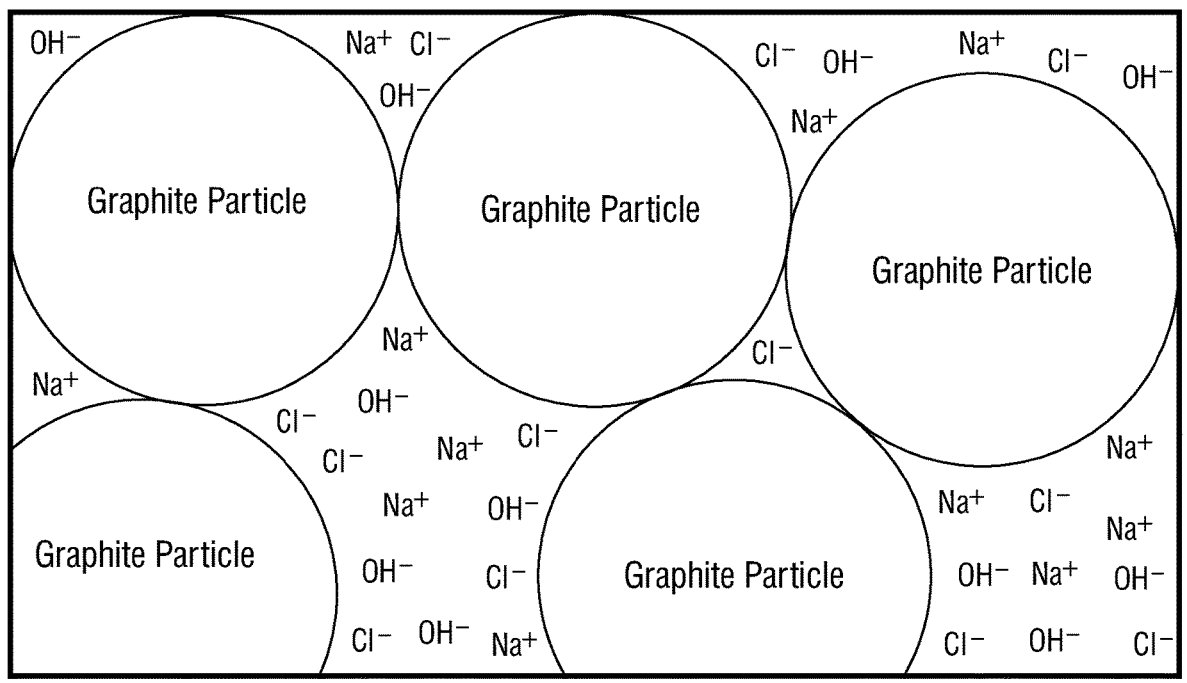

*Fig.4*

GRAPHITE POWDER BASED COUNTER ELECTRODE

CROSS-REFERENCE TO RELATED APPLICATIONS

This application is a Nonprovisional Application of U.S. Provisional Application No. 62/758,288, filed Nov. 12, 2018, the disclosure of which is incorporated herein by reference.

FIELD OF INVENTION

This invention is directed to a counter electrode. More specifically, this invention relates to a graphite powder based counter electrode.

BACKGROUND OF INVENTION

Metal implants are used in patients with many different injuries or medical problems. In particular, metal implants may be used for any individual that needs to replace a missing body part. For example, a metal implant may be used to replace a patient's hips or knees. One potential problem with metal implants is that they tend to allow for the growth of bacteria on the surface. This may increase the patient's risk for an infection. To decrease the risk of infection, electrodes can provide electrical stimulation to disrupt the growth of bacteria.

In particular, electrodes are well suited for applying a type of electrical stimulation called cathodic voltage to a metal implant. This technique is called cathodic voltage controlled electrical stimulation ("CVCES") and it works by disrupting bacteria from growing on the metal implant.

CVCES is generated by way of an electrochemical process. Many electrochemical processes use what is referred to as a three-electrode system in order to elicit a reduction-oxidation reaction, or redox reaction. In addition to providing an antibacterial environment on metal implants, redox reactions can be used to control processes such as metal extraction, battery outputs, production of chemicals, and electroplating. All of these processes require at least two electrodes. The first electrode is often referred to as a working electrode, which represents a metal of interest, and the second electrode is often referred to as a counter electrode, which is used to pass current to the working electrode. Counter electrodes are often made from materials that are electrochemically inert and highly conductive such as gold, platinum, and carbon.

The use of electrodes required by the CVCES technique can be difficult because of the anatomical and physiological make-up of the body. It is preferred that when applying CVCES to a metal implant, the surface area of the counter electrode (the anode) is at least the same as the surface of the working electrode (the cathode), preferably twice the surface area.

Metal implants can have high surface area and thus would typically require a massive plate-based skin electrode or an implanted mesh to facilitate the redox reaction. As can be imagined, large gold and platinum counter electrodes are often cost prohibitive. Thus, carbon counter electrodes may reduce the cost. There are several versions of carbon rubber skin electrodes currently on the market that could be used for CVCES; however, these counter electrodes have several drawbacks as they are intended for other medical applications.

Due to the nature of the CVCES redox reaction, standard carbon rubber electrodes cannot prevent acidic build-up on the skin that will occur. As the cathode builds a highly alkaline pH local environment, the anode builds an acidic environment, which can reach pH levels less than 1 depending on the starting pH and the amount of current passed through the environment. Carbon rubber skin electrodes are also limited to their 2-dimensional surface area to facilitate the redox reaction due to the fact that only the outer carbon particles come into contact with the electrolyte needed for the redox reaction; thus, several counter electrodes (anodes) will be required for large metal implant treatments. Implantable meshes have shown efficacy in small animal models but are virtually not an option in clinical settings due to the invasive procedures required to implant a mesh with suitable surface area.

Thus, there is a need for a better counter electrode in order to improve CVCES by avoiding the above mentioned problems.

SUMMARY OF THE INVENTION

Accordingly, it is the subject of this invention to provide an improved counter electrode that is particularly suited for use in CVCES. The invention disclosed herein is a novel, carbon-based, counter electrode that is intended to provide superior conduction and performance for an array of redox reaction applications.

In one embodiment, the present invention provides a device comprising a housing having a lead opening; a counter electrode contained within the housing and wherein the counter electrode further includes graphite powder, electrolyte gel, and a base; a potentiostat that is connected to the counter electrode by way of a metallic wire or metallic rod that extends through the lead opening into the counter electrode; and a hydrogel having a first and second side and wherein the housing and counter electrode are mounted onto the hydrogel.

In this embodiment, the skin-based counter electrode having a graphite powder suspended in an electrolyte gel overcomes the aforementioned problems. This counter electrode maintains electrochemical conduction with the metal implant through the skin and allows the system to be minimally invasive.

When using the device of the present invention, the skin should be cleaned and hydrated to provide optimal conduction, because hair, foreign particles, or residues on the skin could reduce conduction capabilities between the counter electrode and the metal implant. Additionally, contaminants will reduce the effective surface area of the counter electrode. The interface between the skin and the counter electrode is a thin hydrogel layer that adheres to the skin. Guarding the counter electrode from the skin with a hydrogel provides biocompatibility and skin protection without sacrificing conduction.

Using a counter electrode that is a powder-based anode suspended in an electrolyte gel allows for an extremely enhanced or massive surface area, thus allowing the counter electrode to maintain a small size while facilitating the current to a large surface area implant. The electrolyte gel is essential to the counter electrode as it provides suspension for the powder while also allowing electrical conduction between the individual grains of graphite so that the particles' surfaces can all participate in the chemical reaction. Using a graphite powder, an allotrope of carbon, provides an anodic material that is both inexpensive and safe in terms of minimal byproducts from corrosion. During the manufacturing of the graphite gel that forms the counter electrode, the pH is adjusted to become highly alkaline. By adjusting the pH of the electrolyte gel to a higher value than neutral, such as 13 (thirteen) which is the preferred embodiment, the acidic effects of the reaction will reduce the pH to a normal and safe level on the skin.

In other preferred embodiments, the pH level can be about 13. Without this feature, patients would likely experience acidic burns at the skin-hydrogel interface due to the duration of the treatment being performed at necessary electric current levels. However, because the graphite gel of the counter electrode is guarded by a hydrogel, the skin will not feel any adverse effects from the highly alkaline starting pH. Only when the reaction causes the pH within the electrolyte gel to go below a neutral threshold will the pH of the hydrogel also begin to decrease to an acidic level. The electrode (anode) also has a non-metallic, such as plastic, backing that adheres or attaches to the hydrogel, thus encapsulating the graphite-powder gel, keeping the gel moist, fluid, and hydrated.

One of the challenges associated with this was determining which electrolyte to use and the ratio of the graphite powder to said electrolyte. When first developing the counter electrode (graphite anode), the electrolyte substance was under consideration. Initially, a phosphate buffer saline was used as the electrolyte substance to electrochemically join the graphite particles. However, it was found that this substance failed to keep the graphite particles properly suspended and homogeneous in the solution. After exploring other options, an electrolyte gel typically used for increasing conduction to the body in traditional electrodes was selected due to its ability to keep the powder suspended and homogeneous. The gel itself is commercially available and is also biocompatible.

In order to properly assess the functionality of the electrode, an electrochemical cell had to be invented to simulate the body in terms of tissue structure, skin, and electrical conductivity. To assess how this could be done, a phantom leg was produced that encapsulated an array of titanium and cobalt-chrome implants that are commonly used in joint replacement surgery. The phantom leg was composed of several components to mimic the body's natural characteristics. Lab grade gelatin was used to control the elastic modulus of the phantom leg to resemble soft tissue, propylene glycol to control thermal conductivity, NaCl to control electrical conductivity (one of the most important factors), deionized water to hydrate the gelling agent, and sodium propionate to prevent bacterial growth. Using a potentiostat, CVCES could then be applied to the metallic implants (the working electrode) while the counter electrode or (skin electrode) was adhered to a sample of pig skin that had been sealed to the surface of the phantom leg. The pig skin was essential because it further adds to the validity of simulation and allowed assessment of effects of the treatment on skin.

Another challenge that had to be overcome was to determine a concentration of sodium hydroxide that would effectively increase the pH to 13 or about 13. To address this challenge, a mathematical formula was used along with one assumption. First a 0.2M solution of NaOH was made. 250 mL of that was mixed with 250 g of electrolyte gel until homogeneous. The assumption was that 250 g of electrolyte gel is the equivalent to 250 g, thus 250 mL, of water, therefore making a 0.1M solution of NaOH. To calculate pH, the formula $pOH=-\log[OH^-]$ was applied. Working through, $-\log[0.1]=1$. Next, the formula $pH+pOH=14$ was applied, solving for a pH of 13. This pH level proved sufficient throughout testing.

There was also a need to create a biocompatible enclosure that kept the graphite gel of the counter electrode hydrated and away from the skin while still allowing for effective adhesion and reaction facilitation. A full enclosure or housing was created to surround the gel to keep it from drying out. Several different form factors and material have been implemented as an enclosure or housing for the graphite gel of the counter electrode throughout the design process. It was determined that no metal can be used in the counter electrode that could come in electrochemical contact with the graphite gel of the counter electrode due to undesirable reduction reactions that take place that either corrode the metal or the gel. As one side of the counter electrode needs to be composed of a hydrogel for skin adhesion, protection and electrical conduction, the backing material is still being considered. In one embodiment the backing material is a rigid plastic resistant to both alkaline and acidic environments.

Hydrogels are very absorbent materials. When the graphite gel is loaded into the counter electrode, the hydrogel barrier absorbs some of the water content from the electrolyte gel. When this occurs, the outside of the hydrogel has a tendency to increase in PH to a higher level. This phenomenon only occurs after the counter electrode has sat for several days. The pH does not increase as high as the electrolyte gel within.

To prevent the hydrogel from absorbing the electrolyte gel's water content and pH levels, the two components need to be stored separately. The container of graphite gel possesses an air tight cap that keeps the gel protected prior to application to the hydrogel. The components could then be combined directly before the application. This can be done with removable mechanical barriers, filling ports, and other suitable barriers know known or developed in the future.

Alternatives to what is described above are not without problems.

The first alternative to using the described graphite powder skin counter electrode would be an implantable counter electrode mesh. This approach is clinically irrelevant but is seen in multiple in-vivo CVCES studies done with animals. This would require a large mesh to be surgically embedded in the surrounding tissue proximal to the metal implant to provide the needed platform for the oxidation half-reaction. Due to biocompatibility and electrochemical reasons, the material would have to be made of a platinum material. Other conductive metals such as carbon, silver, and copper have all proven to have harmful effects when in direct contact with internal tissue due to adverse interactions with cellular metabolism. For example, it is known that silver ions can bind with cellular enzymes which can ultimately impact the cell's ability to transport nutrients and synthesize other cellular components, thus killing the cell. Therefore, this alternative would become highly invasive and expensive. In addition to being invasive, using a platinum material in an implanted scenario would expose internal soft tissue to highly acidic byproducts of the redox reaction, further harming the patient. The graphite skin counter electrode disclosed herein allows doctors to take a minimally invasive and cost effective approach to CVCES treatments.

A second alternative to using the above described graphite powder skin counter electrode would be to use an off-the-shelf electrode that already has FDA (United States Food and Drug Administration) clearance. Most electrodes in the medical field are used for sensory applications such as EEGs, EMGs, and ECGs, or for electrical stimulation applications such as TENS. Due to their lack of metallic surface area, sensory electrodes would not be suitable to facilitate a CVCES treatment. However, it has been shown that some select electrical stimulation electrodes, specifically carbonized rubber electrodes, can work to facilitate a CVCES treatment. This is due to their larger surface area and carbon composition which provides a good anodic platform for the reaction. This electrode requires a coating of electrolyte gel to be applied at the skin-electrode interface to promote proper electrical conduction.

There are several reasons why this alternative would be less suitable for this application. First, this electrode has no means of protection against acidic pH changes on the skin because it is not intended to be used as an electrochemical anode, rather it is used solely as a means to pass current to another skin electrode. Due to the redox reaction that takes place, the pH of the electrolyte gel that was applied to the electrode will decrease to unsafe levels which could possibly cause acidic burns on the skin. This electrolyte gel cannot be pH adjusted as the above described graphite powder skin counter electrode already is, because altering the gels composition invalidates its FDA clearance.

Another downside to this approach is that because this electrode is a solid pad of rubberized carbon, it lacks the surface area preferred to facilitate the CVCES reaction on full sized implants. As mentioned, the above described graphite powder skin counter electrode is a composition that includes a powder suspended in an electrolyte gel which allows for more than enough surface area to facilitate the reaction.

It should be made clear that common carbon rubber electrodes are also manufactured using powder-like carbon particles that have been polymerized within the rubber body of the electrode. However, rubber is not an electrolyte and only the carbon particles that are exposed to the electrolyte gel applied to the electrode surface can participate in the redox reaction. Particles encapsulated by the rubber serve purely as an electrical connection as opposed to the particles exposed to the electrolyte which serve as an electrochemical platform. Therefore, carbon rubber electrodes are viewed only as a 2-dimensional anodic surface.

A third alternative are custom skin electrodes made from alternative materials such as silver, copper, or stainless steel. These electrodes consist of a plate style surface made of the alternative material. The issue with using materials that are not electrochemically inert as an anode is that the oxidative reaction that will ultimately occur at that surface may produce unwanted or toxic byproducts that may change how the device functions, drifts the current levels passing through the system, or cause irritation to the patient's skin. Platinum and carbon are electrochemically inert metals, meaning they do not form byproducts from oxidation. While platinum itself can be used, by itself, carbon offers a larger surface area as you can build a large powder-based electrode.

The counter electrode disclosed herein, solves the above problems. The counter electrode is comprised of graphite powder, electrolyte gel, and NaOh.

BRIEF DESCRIPTION OF THE DRAWINGS

FIG. 3 is a table that depicts instructions.
FIG. 4 is a depiction of a graphite powder gel composition.

DETAILED DESCRIPTION OF THE INVENTION

In one embodiment, a graphite powder device is provided. For electrochemical processes to occur, there must be an anode and a cathode within an electrolyte solution. The anode is a metallic surface where oxidative reactions occur, and the cathode is another metallic surface where reduction reactions occur. A reduction reaction is essentially when the material of interest gains electrons and thereby decreases the oxidation state of the molecules. The electrolyte that the anode and cathode each reside in provides the electrical connection by facilitating the flow of electrons shuttled by ion carriers such as sodium or potassium ions. Electrons are driven from the anode to the cathode through the electrical path via a potentiostat. A potentiostat is an instrument used to drive current from a counter electrode to a working electrode in order to keep the voltage on the working electrode at a constant value compared to a stable reference electrode.

In the case of Cathodic Voltage Controlled Electrical Stimulation (or CVCES), the anode represents the counter electrode and the cathode represents the working electrode. Using a potentiostat, a user can dictate which electrochemical process is actually occurring on the working electrode and at what rate it occurs simply by adjusting the applied voltage parameters. The counter electrode has specific physical, electrical, and chemical requirements that it must meet in order to sufficiently facilitate CVCES, especially in a clinical environment when a patient's health is concerned.

Figure 1:
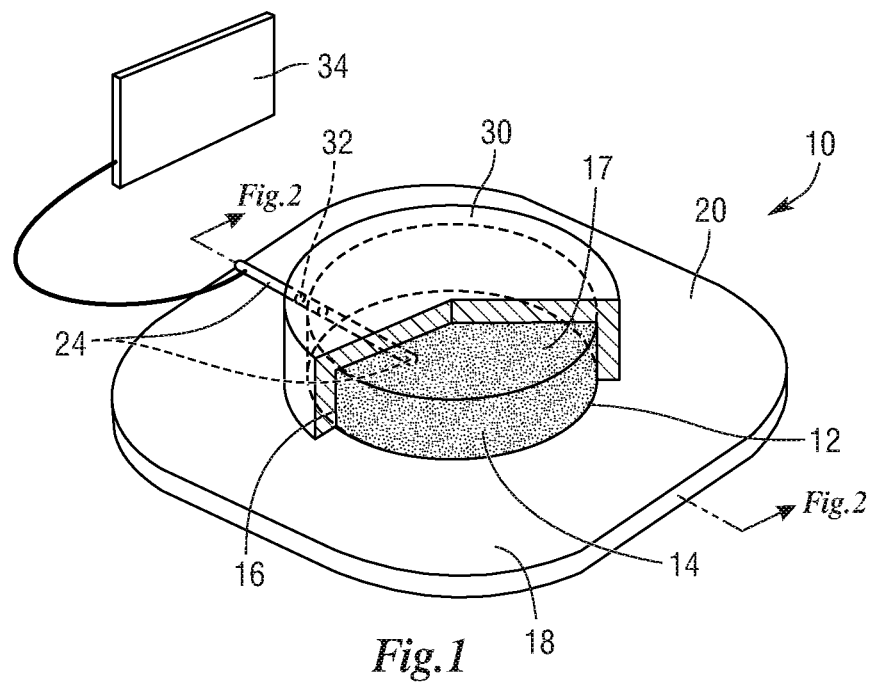
FIG. 1 is an isometric view of the device.
Figure 2:
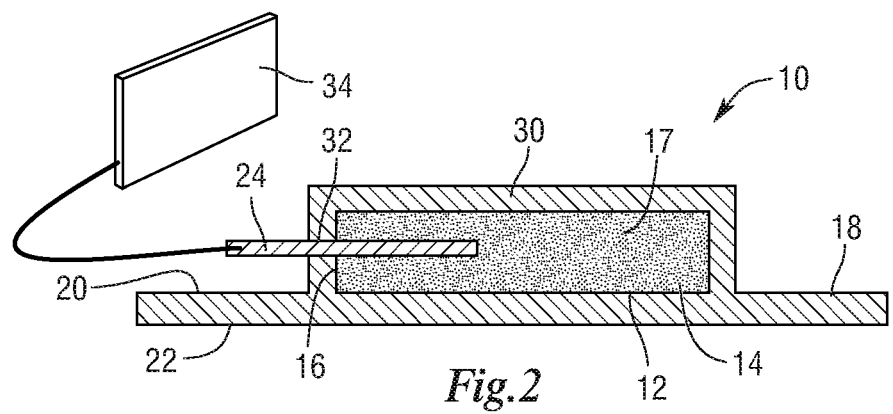
FIG. 2 is a cross section of the device.

The CVCES technique in a clinical setting has been shown as a way to fight bacterial biofilm infections on metallic implants in the most minimally invasive way possible. In this setting the bodies of the patients act as an electrochemical cell by using the metal implant as the cathode and another electrode as the anode. Therefore, as shown in FIGS. 1 and 2, a device 10 has been invented that fulfills all the requirements of having proper skin electrical conductivity while still being minimally invasive by adhering to the patient's skin and that also implements safety measurements that off-the-shelf electrode options do not have.

This device 10 includes a graphite powder-based skin electrode (also called a working electrode) 12 that is composed of graphite powder 14 suspended in an electrolyte gel 16 that allows for electrochemical conduction between the particles of graphite powder 14. The ratio of graphite powder 14 measured in grams to electrolyte gel 16 measured in grams can be anywhere from 1:2 to 1:100. In one embodiment the ratio is 1:10. In one embodiment, the electrolyte gel is commercially available from Parker Labs and is sold as Signs Gel. In other embodiments, any suitable commercially available electrolyte gel can be used.

In one embodiment, the particle size of graphite powder 14 is in the range of 0.037 mm to 2 mm. Powder particle size is often referred to as "mesh size". The mesh size of the powder in a preferred embodiment is in the range of 4 to 400, more preferably, the mesh size is 200.

The pH of electrolyte gel 16 is adjusted to an alkaline value to counteract the acidic environment that is produced at the anode 12 as a result of the oxidation reaction. The pH of electrolyte gel 16 is adjustable and can range from 9 to 15, and in one of the embodiments the pH is 13. The electrolyte gel 16 is spread over a first side 20 of a hydrogel 18 (also referred to as hydrogel layer 18). The hydrogel layer 18 is a macromolecular polymer gel constructed of a network of crosslinked polymer chains. Hydrogels have high water content that allows them to facilitate electrochemical conduction throughout its body. The hydrogel 18 has an opposed second side 22 that adheres to a patient's skin (not shown). Ideally, the hydrogel 18 protects the skin from the initially high alkaline levels in hydrogel 18; however, if the hydrogel 18 is in contact with the electrolyte gel 16 for an extended period of time the pH of the hydrogel 18 will increase due to its ability to absorb the electrolyte's water content.

This phenomenon can be minimized by keeping the components separated until it is time for application. During treatment, the pH of hydrogel 18 will only begin to reduce once the pH of the anodic graphite gel within it reduces to a level below the pH of hydrogel 18. Without intending to be bound by theory, this is because the electrochemical reaction only takes place within the gel's electrolyte, at the graphite particle's surface-electrolyte interface. So, once the electrolyte has a concentration of protons (created by the electrochemical reaction on the graphite) greater than that of the hydrogel 18, the spatial range of those excess protons will flood through the hydrogel 18, thus decreasing its pH. Due to the initial pH adjustment, this event will occur hours after use, therefore limiting risk of acidic burn to the patient.

The counter electrode 12 is preferred to have at least the same amount of surface area as the working electrode, preferably twice as much. This is due to the fact that the reduction reaction at the cathode consumes a certain number of electrons and thus the anode must have enough surface area to produce as many electrons that are being consumed. If the surface area requirement is not met, the potentiostat will increase its voltage to the counter electrode 12 to increase the current density at its surface, thus creating higher and more intensified chemical species reaction than at the cathode. This increased ratio of acidic chemical species may cause the electrode to neutralize the pH adjustment faster than anticipated and could lead to harm to the skin. Some of the chemical species created at the anode 12 surface may be evolved gasses.

Gas build-up within the electrode may create a pressurization that will require a means of expansion in the housing 30 or an outgassing mechanism. When considering a clinical setting, securing enough surface area of an anode on the outside of the body is difficult with current electrodes due to how large the surface area of many 3-dimensional metallic implants (not shown) have become. The surface area of some metallic implants, for example a femoral stem and acetabular head for a hip replacement, can have a surface area as high as $30"^2$. Many implants contain sintered metallic beads on their surfaces to promote osseointegration and consequently increase the surface area even further. As such, the amount of 2-dimensional electrode surfaces required would become very cumbersome to the patient.

The graphite powder-based skin electrode 12 described herein shows that the powder-based anode 12 allows for a massive surface area that is dependent on the volume of the gel as opposed to the outer perimeter area. This unique approach allows the electrode size to be condensed to a much smaller area on the patient's skin which ultimately improves patient comfort and compliance while also maintaining its minimally invasive approach and eliminating the need for an implanted device.

Most electrodes in the medical field are used for sensory applications such as EEGs, EMGs, and ECGs, or for electrical stimulation applications such as TENS. Due to their lack of metallic surface area, sensory electrodes would not be suitable to facilitate a CVCES treatment. However, it has been shown that some select electrical stimulation electrodes, specifically carbonized rubber electrodes, can work to facilitate a CVCES treatment. This is due to their larger surface area and carbon composition which provides a good anodic platform for the reaction. This electrode requires a coating of electrolyte gel to be applied at the skin-electrode interface to promote proper electrical conduction.

There are several reasons why the sensory electrode alternative would be less suitable for a CVCES application. First, this type of electrode has no means of protection against acidic pH changes on the skin because it is not intended to be used as an electrochemical anode, just as a means to pass current to another skin electrode. Due to the redox reaction that takes place, the pH of the electrolyte gel that was applied to the electrode will decrease to unsafe levels which could possibly cause acidic burns on the skin. This electrolyte gel cannot be pH adjusted as the powder-based skin electrode 12 of the present disclosure is because altering the gels composition invalidates its FDA clearance. Another downside to this approach is that because this electrode is a solid pad of rubberized carbon, it lacks the surface area required to facilitate the CVCES reaction on full-sized implants. As mentioned, the device 10 disclosed herein is a skin electrode 12 having graphite powder 14 suspended in an electrolyte gel 16 that allows for more than enough surface area to facilitate the reaction. It is noted that common carbon rubber electrodes are also manufactured using powder-like carbon particles that have been polymerized within the rubber body of the electrode. However, rubber is not an electrolyte and only the carbon particles that are exposed to the electrolyte gel applied to the electrode surface can participate in the redox reaction.

In a sensory electrode, particles encapsulated by the rubber serve purely as an electrical connection as opposed to the particles exposed to the electrolyte which serve as an electrochemical platform (as in device 10). Therefore, carbon rubber electrodes are viewed only as a 2-dimensional anodic surface.

Chemical composition is another significant factor when considering an anodic counter electrode material. Counter electrodes are typically fabricated from electrochemically inert materials such as platinum, gold, and carbon. During a cathodic voltage stimulation to the working electrode, these materials do not readily form oxidation layers on their surface as do some materials such as silver, which ultimately keeps the reaction stable and the charge transfer processes consistent. With these materials in mind, carbon was selected for use in the graphite powder-based skin electrode 12 due to its excellent conductive comparability to the other precious metal materials, lack of corrosion byproducts, low cost, and importantly its availability as a powder which, as previously mentioned, is a one of the key attributes to this electrode's 12 efficacy.

Graphite powder, an allotrope of carbon was ultimately selected for use in the electrode. As mentioned, electrolyte gel 16 is typically used as an electrical conduction medium for other electrodes was used to suspend the graphite powder 14 while also allowing each individual particle to electrically conduct with each other. In one of the embodiments, the ions in the electrolyte gel 16 are sodium and potassium ions; however, any conductive, non-toxic electrolytes may also be used.

The device 10 further includes a device housing 30 mounted on the hydrogel layer 18. The device housing 30 contains the electrolyte gel 16 and graphite powder 14, and the device housing 30 defines an opening or lead opening 32. As mentioned, when talking about chemical species build-up such as gas within the housing 30, the housing 30 includes a mechanism to vent the gas into an extension chamber (not shown), or directly into the air. In the case of an extension container, this component has a reservoir of open space that allows the gas to pressurize within as opposed to building up within the main housing 30 and popping through the hydrogel side 18. This component would be attached to the housing at the time of application. Both the graphite gel housing 30 and the extension chamber must be made of a chemically resistant plastic so as to prevent degradation of the housing during storage.

To electrically connect the gel 16 to the potentiostat 34, a metallic wire or rod 24 that may be solid extends through the opening 24 and is embedded in the electrolyte gel 16. A portion of the metallic wire or rod 24 protrudes from the device housing 30 such that it protrudes from the graphite powder-based skin electrode 12. The metallic wire or rod 24 connects to a potentiostat 34. Potentiostats are well known and their use and operation are well known to those having ordinary skill in the art. It is important that the embedded metallic wire or rod 24 be made of a material that can act as a counter electrode itself, because when touching the electrolyte gel 16, it becomes a part of the electrochemical reaction. Materials such as gold, platinum, silver, or solid graphite can be used. Carbon is not preferred for this thin wire component due to its brittleness in solid state, but could be adapted into a rod component that demonstrates better mechanical properties. Silver is typically not recommended for the overall counter electrode due to the oxide it builds but since this wire component contributes such a small percentage of the total counter electrode surface area, it would be sufficient for this component.

Testing has shown that when applying cathodic voltages that are necessary to effectively remove biofilms from metallic implants, the amount of current that must transfer through the system can reach as high as 500 milliamps. Also, the treatment time necessary to effectively remove biofilms completely from metallic implants can take up to 24 hours. When these quantities of current are transferred through the electrochemical cell for several hours, the amount of protons that build up around the counter electrode as an electrochemical byproduct can decrease the pH of the gel electrolyte 16 to as low as 1 on the pH scale, assuming that the gel electrolyte 16 begins at a neutral pH. This highly acidic pH change may cause a risk to the patient's skin and cause irritation, rash, or even burning of the patient's skin where the electrode 12 is placed.

This is an issue that normally could not be addressed if using a typical carbon-rubber electrode because the electrode has no mechanism to counteract the pH that occurs in this specific reaction. However, the graphite powder skin electrode 12 is created with an increased pH through mixing specific concentrations of any strong base, for example sodium hydroxide (NaOH) in a preferred embodiment, into the electrolyte gel 16. NaOH is a strong base, meaning that the molecule completely ionizes in solution into NA+ and OH− molecules. The increased concentration of OH− molecules, or hydroxide ions, is what is responsible for an increase in pH to a highly alkaline environment. The graphite powder 14 suspended in an electrolyte gel 16 forms a graphite powder gel 17 that is now highly alkaline. As such, the reduction oxidation reaction in the electrochemical cell will naturally neutralize the alkaline environment to a neutral pH that is safe for human skin. Essentially the electrode will start at a high pH, preferably near 13, and will be lowered to between 3 and 5 as opposed to as low as 1, depending on the length of the treatment and the surface area of the implant (working electrode).

Since the pH scale is a logarithmic scale, these results are several orders of magnitudes safer for the patient's skin. It is noted that, alkaline environments can also be harmful to human skin. However, there is the hydrogel layer 18 that separates the graphite powder gel 17 from the patient's skin, while also maintaining proper conduction. The pH of the hydrogel layer 18 is neutral and thus provides a safe contact for the skin. Since the reaction takes place in the graphite powder gel 17, the pH of the hydrogel layer 18 will only decrease once the pH environment within the graphite powder gel 17 has decreased below the initial pH of the hydrogel layer 18. If the graphite powder gel 17 did not contain any sodium hydroxide, the pH of the hydrogel layer 18 would decrease to 1 at the same rate as the graphite powder gel 17. The graphite powder gel 17 in the device housing 30 is enclosed by the hydrogel layer 18 on the contact side or first side 20 of a hydrogel layer 18 and a plastic backing that does not degrade under extreme pH environments. Sealing the gel from the air keeps it moist and preserved.

FIG. 3. is a table that lists the ingredient, preferred amounts, and instructions for all components that make up the graphite powder gel 17 that resides within the graphite powder-based skin electrode 12 used for applying cathodic voltages to metallic implants.

FIG. 4 depicts the graphite powder gel 17 composition, which is comprised of graphite powder 14 and electrolyte gel 16 and a strong base. The graphite powder 14 is a homogenous distribution with the electrolyte gel 16. Graphite powder gel 17 includes graphite particles, Na+ ions, Cl− ions, and OH− ions.

EXAMPLES

Example 1

As shown in the table depicted in FIG. 3, a solution of NaOH was created by dissolving NaOH beads or crystals into deionized water. Aqueous NaOH solutions may also be used. The concentration of NaOH can range from 0.1M to 1.0M, but in an ideal embodiment the concentration should be 0.2M. This solution is then placed on a mixing hotplate and heated until warm, approximately 40-60 degrees Celsius. For every 25 mL of 0.2M NaOH that is prepared, 1 gram of lab grade gelatin is added to the solution. The solution then continues to mix while the gelatin is allowed to hydrate for approximately 1 hour. The gelatin is used to stiffen the NaOH-gel mixture as it becomes less viscous in the next step. While the gelatin is hydrating, a certain amount of off-the-shelf electrolyte gel is added to an automatic mixing bowl that allows for heating mixtures. The gel is heated and stirred until it is at the same temperature as the NaOH solution. Once the gelatin is hydrated, the solution can be added to the mixing bowl with the electrolyte gel. The number of milliliters of NaOH solution needs to be equal to the number of grams of electrolyte gel. The mixture is stirred at constant warm temperature until fully homogeneous. At this point in the process, pure graphite powder can be mixed into the gel.

In the preferred embodiment, the number of grams of graphite powder should be equal to 1/10th the number of grams of electrolyte gel originally used in the mixture. Once the graphite powder is fully homogenized into the mixture, the mixture can be poured into the chemically resistant plastic housings and then sealed with a cap. The metallic wire or rod has been preinstalled in the housing before pouring of the gel for electrical connection to the potentiostat or power supply. This wire or rod can be made from any acceptable counter electrode material, but in a preferred embodiment the wire should be made from platinum. When ready for application, the housing's cap is removed and the housing is attached to a hydrogel thus sealing the graphite gel to prevent any evaporation and providing a barrier between the graphite gel and the skin.

The theoretical calculation for the pH of the final gel is based on the assumption that 1 gram of electrolyte gel is equivalent to 1 gram and thus 1 mL of water once the gel and the NaOH solution are mixed. To calculate the electrodes pH after fabrication the following formula applied:

$$pOH = -\log[OH-]$$

Where if 0.2M NaOH is mixed with electrolyte gel in an equal mL/gram ratio, the concentration then becomes 0.1M. Work out that $-\log[0.1] = 1$. Next, the following formula was applied:

$$pH + pOH = 14$$

By isolating the pH variable, it was determined that the final theoretical pH of the graphite gel is 13.

It will be appreciated by those skilled in the art that while the device 10 having a graphite powder based skin electrode 12 has been described in detail herein, the invention is not necessarily so limited and other examples, embodiments, uses, modifications, and departures from the embodiments, examples, uses, and modifications may be made without departing from the process and all such embodiments are intended to be within the scope and spirit of the appended claims.

What is claimed is:

1. A device configured for administering biofilm treatment to an infected orthopedic implant, the device comprising:
    a housing including a lead opening;
    a counter electrode disposed in the housing, wherein the counter electrode is comprised of particles of a graphite powder suspended in an electrolytic gel and a base, enabling the counter electrode to have a highly alkaline pH;
    a potentiostat capable of providing a cathodic voltage to the infected orthopedic implant;
    a metallic wire or metallic rod connecting the potentiostat to the counter electrode through the lead opening of the housing wherein the counter electrode forms an anode of an electrochemical cell; and
    a hydrogel layer disposed beneath the counter electrode and configured for skin attachment in relation to the orthopedic implant.

2. The device of claim 1, wherein the housing is made of a plastic.

3. The device of claim 2, wherein the metallic wire or metallic rod is made of gold, silver, graphite, or platinum.

4. The device of claim 3, wherein the metallic wire or metallic rod is made of platinum.

5. The device of claim 1, wherein the counter electrode is further comprised of NaOH, which is used as the base.

6. The device of claim 1, wherein the particles of graphite powder are between 0.037 mm and 2.0 mm in size.

7. The device of claim 5, wherein the concentration of NaOH is between 0.1 M and 1.0 M.

8. The device of claim 6, wherein the concentration of NaOH is 0.2 M.

9. The device of claim 1, wherein the pH of the counter electrode is at least 13.

10. The device of claim 1, further comprising means for venting acidic byproducts into a separate chamber or into the environment.

11. The device of claim 10, wherein the separate chamber is disposed as part of the housing or separate from the housing.

12. The device of claim 10, wherein the separate chamber is made of plastic.

13. The device of claim 1, wherein the counter electrode further includes a gelatin.

* * * * *